(12) United States Patent
Anderson

(10) Patent No.: US 8,429,186 B2
(45) Date of Patent: Apr. 23, 2013

(54) SYSTEM AND METHOD FOR RAPID ASSESSMENT OF LAB VALUE DISTRIBUTIONS

(75) Inventor: David R. Anderson, Chaska, MN (US)

(73) Assignee: OptumInsight, Inc., Eden Prairie, MN (US)

( * ) Notice: Subject to any disclaimer, the term of this patent is extended or adjusted under 35 U.S.C. 154(b) by 155 days.

(21) Appl. No.: 12/774,270

(22) Filed: May 5, 2010

(65) Prior Publication Data

US 2010/0287190 A1 Nov. 11, 2010

Related U.S. Application Data

(60) Provisional application No. 61/175,538, filed on May 5, 2009.

(51) Int. Cl.
*G06F 17/30* (2006.01)

(52) U.S. Cl.
USPC .................................. 707/769; 705/2; 705/3

(58) Field of Classification Search .............. 707/769
See application file for complete search history.

(56) References Cited

U.S. PATENT DOCUMENTS

| | | | |
|---|---|---|---|
| 7,979,290 B2 * | 7/2011 | Dang .................................. | 705/3 |
| 2003/0046114 A1 | 3/2003 | Davies et al. ..................... | 705/3 |
| 2004/0220831 A1 * | 11/2004 | Fabricant .......................... | 705/2 |
| 2005/0004895 A1 * | 1/2005 | Schurenberg et al. ............ | 707/3 |
| 2006/0190295 A1 * | 8/2006 | Merkin .............................. | 705/2 |
| 2006/0234196 A1 | 10/2006 | Novatzky et al. ............. | 434/262 |
| 2007/0016442 A1 * | 1/2007 | Stroup .............................. | 705/2 |
| 2007/0185734 A1 * | 8/2007 | Palsbo et al. ..................... | 705/2 |
| 2007/0198301 A1 * | 8/2007 | Ayers et al. ...................... | 705/3 |
| 2008/0077443 A1 * | 3/2008 | Singer .............................. | 705/3 |
| 2008/0201172 A1 | 8/2008 | McNamar ......................... | 705/3 |
| 2008/0228716 A1 * | 9/2008 | Dettinger et al. ................. | 707/3 |
| 2008/0275732 A1 * | 11/2008 | Falchuk et al. ................... | 705/3 |
| 2008/0294692 A1 | 11/2008 | Angell et al. ........................ | 1/1 |
| 2009/0076845 A1 * | 3/2009 | Bellin et al. ...................... | 705/2 |
| 2009/0080734 A1 | 3/2009 | Moriya et al. ................ | 382/128 |
| 2010/0205141 A1 * | 8/2010 | Meesa .......................... | 707/602 |
| 2010/0325148 A1 * | 12/2010 | Anderson ..................... | 707/769 |
| 2011/0125531 A1 * | 5/2011 | Seare et al. ....................... | 705/3 |

OTHER PUBLICATIONS

International Search Report issued in corresponding application PCT/US10/33695, mailed Jun. 28, 2010.

* cited by examiner

*Primary Examiner* — Binh V Ho
(74) *Attorney, Agent, or Firm* — Fulbright & Jaworski, LLP

(57) ABSTRACT

System and methods for rapid assessment of lab value distributions are provided. In one embodiment, the system includes a data storage device and a server. The data storage device may be configured to store a database comprising one or more records, wherein the records are identified by one or more test codes. The server may receive a medical code, search the database to obtain a first group of records associated with individuals having the medical code, wherein each record of the first group of records is identified by a test code, search the database to obtain a second group of records associated with a control population, wherein each record of the second group of records is identified by the test code, and generate an output comprising a distribution graph on a shared scale from the first and second group of records.

22 Claims, 15 Drawing Sheets

SYSTEM AND METHOD FOR RAPID ASSESSMENT OF LAB VALUE DISTRIBUTIONS

CROSS-REFERENCE TO RELATED APPLICATIONS

This application claims priority to U.S. Provisional Application No. 61/175,538 filed May 5, 2009, the entire contents of which is specifically incorporated herein by reference without disclaimer.

BACKGROUND OF THE INVENTION

1. Field of the Invention

This invention relates to health related data analysis and more particularly relates to a system and method for rapid assessment of lab value distributions between comparison groups.

2. Description of the Related Art

Most corporations, including health insurance corporations, maintain a high volume of data. Such data may be analyzed and exploited for valuable information regarding business trends, and other important statistics. Data mining is a common strategy for identifying and analyzing such data.

There are many various forms of data mining. Custom analytic operations may be developed to meet specific needs. Alternatively, commercially available statistical analysis tools, such as Statistical Analysis Software (SAS) may be used to identify statistical trends in data.

Health insurance companies typically maintain databases of health insurance claim information, demographic information, and other data about health insurance plan members. Such information may be used to gain valuable insights into early disease diagnosis, relationship between lab tests and diseases or drug treatments, and disease severity. Unfortunately, typical methods for analyzing such data are often cumbersome, costly, and require unworkably high processing times and resources.

The referenced shortcomings are not intended to be exhaustive, but rather are among many that tend to impair the effectiveness of previously known techniques in disease management, diagnosis and treatment; however, those mentioned here are sufficient to demonstrate that the methodologies appearing in the art have not been satisfactory and that a significant need exists for the techniques described and claimed in this disclosure.

SUMMARY OF THE INVENTION

From the foregoing discussion, it should be apparent that a need exists for a system and method to rapidly analyze, discover, and summarize differences in lab value distribution between comparison groups, particularly in any temporal context of any temporal attribute.

A system is presented for rapid assessment of lab value distributions. In one embodiment, the system includes a data storage device configured to store a database comprising one or more records, wherein the records are identified by one or more test codes. The system may also include a server in data communication with the data storage device. The server may be suitably programmed to receive a medical code (where lab values may include a range of interest), search the database to obtain a first group of records associated with individuals having the medical code, wherein each record of the first group of records is identified by a test code, search the database to obtain a second group of records associated with a control population, wherein each record of the second group of records is identified by the test code, and generate an output comprising a distribution graph on a shared scale from the first and second group of records.

In one embodiment, the server may compare a first value representing the first group and a second value representing the second group of records. In a further embodiment, the server may interpolate the first group of records to obtain the first value and to interpolate the second group of records to obtain the second value, wherein the first and second values are associated with a shared percentile, such as 5%, 32%, 50%, 95%, or any intermediate percentile. For example, values of median in both groups may be compared.

In a certain embodiment, the server may count distinct records in the first group of records and the second group of records. The server may also aggregate records from the first group and from the second group according to a selected attribute, such as a selected range of test values, and/or compute a probability in response to a ratio of a number of records in the first group having the selected attribute and a number of records in the second group having the selected attribute.

The server may further select the first group of records from within a time interval, such as a time span (e.g., about 30 days) before or after of initial diagnosis or disease onset. In a further embodiment, the server may select records in the first group and in the second group according to a limiting criterion, such as a disease-related parameter.

A method is also presented for comparing two groups of records to analyze their distribution discrepancy. In one embodiment, the method includes receiving a medical code, searching a database stored on a data storage device to obtain a first group of records associated with individuals having the medical code, wherein each record of the first group of records is identified by a test code, searching the database to obtain a second group of records associated with a control population, wherein each record of the second group of records is identified by the test code, and generating an output comprising a distribution graph on a shared scale from the first and second group of records. The method in the disclosed embodiments substantially includes the steps necessary to carry out the functions presented above with respect to the operation of the system of the present invention.

The method may further include comparing a first value representing the first group and a second value representing the second group of records. Additionally, the method may also include interpolating the first group of records to obtain the first value and interpolating the second group of records to obtain the second value, wherein the first and second values are associated with a shared percentile, such as any intermediate percentile from 5%-95%, or. In a particular embodiment, median-associated values may be compared.

In a certain embodiment, the method may include counting distinct records in the first group of records and the second group of records. The method may also include aggregating records from the first group and from the second group according to a selected attribute, such a test value or range. In a still another embodiment, the method may also comprise computing a probability in response to a ratio of a number of records in the first group having the selected attribute and a number of records in the second group having the selected attribute.

To process records at any temporal interval related to a disease, the method may further comprise selecting the first group of records from within a time interval. Such a time interval may be relative to the date or time of the individual's first occurrence of the disease associated with medical code or the date or time when the individual is first diagnosed. In a still further embodiment, the method may comprise selecting records in the first group and in the second group according to a limiting criterion, such as a disease-related parameter, age, gender, or the like.

There may be also provided a tangible computer program product comprising a computer readable medium having computer usable program code executable to perform operations comprising: receiving a medical code; searching a database stored on a data storage device to obtain a first group of records associated with individuals having the medical code, wherein each record of the first group of records is identified by a test code; searching the database to obtain a second group of records associated with a control population, wherein each record of the second group of records is identified by the test code; and generating an output comprising a distribution graph on a shared scale from the first and second group of records.

The operations may further include comparing a first value representing the first group and a second value representing the second group of records. Moreover, the operations may include interpolating the first group of records to obtain the first value and interpolating the second group of records to obtain the second value, wherein the first and second values are associated with a shared percentile.

In a certain embodiment, the operations may include counting distinct records in the first group of records and the second group of records. The operations may also include aggregating records from the first group and from the second group according to a selected attribute. In still another embodiment, the operations may also include computing a probability in response to a ratio of a number of records in the first group having the selected attribute and a number of records in the second group having the selected attribute.

For a temporal analysis, the operations may further comprise selecting the first group of records from within a time interval. In a still further embodiment, the operations may also include selecting records in the first group and in the second group according to a limiting criterion, such as a disease-related parameter, age, gender, or the like.

For a record with multiple lab test values, the record could comprise an average, a first reading or a last reading of a test. To further analyze disease-associated parameters, each record in the first group of records may share a limiting criterion with each record in the second group of records, for example, those records in the first and second group may have the same age range, gender, or geographic residence. Furthermore, the control population could be a normal group or a cohort group. In certain aspects, the distribution graph may be a histogram or any format suitable for presenting a distribution.

The term "associated" is referred to as connected or related. The term "coupled" is defined as connected, although not necessarily directly, and not necessarily mechanically.

The terms "a" and "an" are defined as one or more unless this disclosure explicitly requires otherwise.

The term "substantially" and its variations are defined as being largely but not necessarily wholly what is specified as understood by one of ordinary skill in the art, and in one non-limiting embodiment "substantially" refers to ranges within 10%, preferably within 5%, more preferably within 1%, and most preferably within 0.5% of what is specified.

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a method or device that "comprises," "has," "includes" or "contains" one or more steps or elements possesses those one or more steps or elements, but is not limited to possessing only those one or more elements. Likewise, a step of a method or an element of a device that "comprises," "has," "includes" or "contains" one or more features possesses those one or more features, but is not limited to possessing only those one or more features. Furthermore, a device or structure that is configured in a certain way is configured in at least that way, but may also be configured in ways that are not listed.

Other features and associated advantages will become apparent with reference to the following detailed description of specific embodiments in connection with the accompanying drawings.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DETAILED DESCRIPTION

Figure 1:
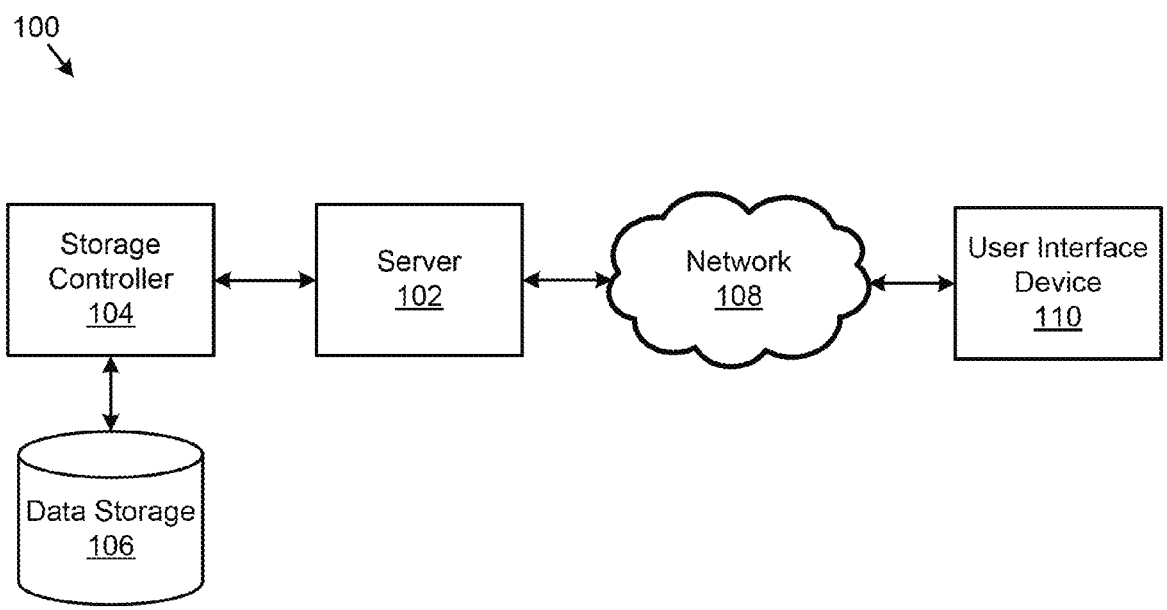
FIG. 1 is a schematic block diagram illustrating one embodiment of a system for rapid assessment of lab value distributions.

Various features and advantageous details are explained more fully with reference to the non-limiting embodiments that are illustrated in the accompanying drawings and detailed in the following description. Descriptions of well known starting materials, processing techniques, components, and equipment are omitted so as not to unnecessarily obscure the invention in detail. It should be understood, however, that the detailed description and the specific examples, while indicating embodiments of the invention, are given by way of illustration only, and not by way of limitation. Various substitutions, modifications, additions, and/or rearrangements within the spirit and/or scope of the underlying inventive concept will become apparent to those skilled in the art from this disclosure.

Certain units described in this specification have been labeled as modules, in order to more particularly emphasize their implementation independence. A module is "[a] self-contained hardware or software component that interacts with a larger system." Alan Freedman, "The Computer Glossary" 268 (8th ed. 1998). A module comprises a component of a machine, a machine or a plurality of machines that are suitably programmed to operate according to executable instructions. For example, a module may be implemented as a hardware circuit comprising custom VLSI circuits or gate arrays, off-the-shelf semiconductors such as logic chips, transistors, or other discrete components. A module may also be implemented in programmable hardware devices such as field programmable gate arrays, programmable array logic, programmable logic devices, a controller, or the like.

Modules may also include software-defined units or instructions that, when executed by a processing machine or device, retrieve and transform data stored on a data storage device from a first state to a second state. An identified module of executable code may, for instance, comprise one or more physical blocks of computer instructions which may be organized as an object, procedure, or function. Nevertheless, the executables of an identified module need not be physically located together, but may comprise disparate instructions stored in different locations which, when joined logically together, comprise the module, and when executed by the processor, achieve the stated data transformation.

Indeed, a module of executable code may be a single instruction, or many instructions, and may even be distributed over several different code segments, among different programs, and across several memory devices. Similarly, operational data may be identified and illustrated herein within modules, and may be embodied in any suitable form and organized within any suitable type of data structure. The operational data may be collected as a single data set, or may be distributed over different locations including over different storage devices.

In the following description, numerous specific details are provided, such as examples of programming, software modules, user selections, network transactions, database queries, database structures, hardware modules, hardware circuits, hardware chips, etc., to provide a thorough understanding of the present embodiments. One skilled in the relevant art will recognize, however, that the invention may be practiced without one or more of the specific details, or with other methods, components, materials, and so forth. In other instances, well-known structures, materials, or operations are not shown or described in detail to avoid obscuring aspects of the invention.

FIG. 1 illustrates one embodiment of a system 100 for rapid assessment of lab value distributions. The system 100 may include a server 102, a data storage device 104, a network 108, and a user interface device 110. In a further embodiment, the system 100 may include a storage controller 106, or storage server, configured to manage data communications between the data storage device 104, and the server 102 or other components in communication with the network 108. In an alternative embodiment, the storage controller 106 may be coupled to the network 108. In a general embodiment, the system 100 may store databases comprising records, perform searches of those records, and generate outputs in response to information contained in these records. Specifically, the system 100 may receive a medical code (where lab values may include a range of interest) and generate an output based on a first group of records associated with individual having a medical code as compared with a second groups of records of a control population.

In one embodiment, the user interface device 110 is referred to broadly and is intended to encompass a suitable processor-based device such as a desktop computer, a laptop computer, a Personal Digital Assistant (PDA), a mobile communication device or organizer device having access to the network 108. In a further embodiment, the user interface device 110 may access the Internet to access a web application or web service hosted by the server 102 and provide a user interface for enabling a user to enter or receive information. For example, the user may enter a medical code, a test code, a time interval, a limiting criterion, a selected attribute for generating an output, or the like.

The network 108 may facilitate communications of data between the server 102 and the user interface device 110. The network 108 may include any type of communications network including, but not limited to, a direct PC to PC connection, a local area network (LAN), a wide area network (WAN), a modem to modem connection, the Internet, a combination of the above, or any other communications network now known or later developed within the networking arts which permits two or more computers to communicate, one with another.

In one embodiment, the server 102 is suitably programmed to receive a medical code (where lab values may include a range of interest), search the database to obtain a first group of records associated with individuals having the medical code, wherein each record of the first group of records is identified by a test code, search the database to obtain a second group of records associated with a control population, wherein each record of the second group of records is identified by the test code, and generate an output comprising a distribution graph on a shared scale from the first and second group of records. Additionally, the server may access data stored in the data storage device 104 via a Storage Area Network (SAN) connection, a LAN, a data bus, or the like.

The data storage device 104 may include a hard disk, including hard disks arranged in an Redundant Array of Independent Disks (RAID) array, a tape storage drive comprising a magnetic tape data storage device, an optical storage device, or the like. In one embodiment, the data storage device 104 may store health related data, such as insurance claims data, consumer data, or the like. The data may be arranged in a database and accessible through Structured Query Language (SQL) queries, or other data base query languages or operations.

Figure 2:
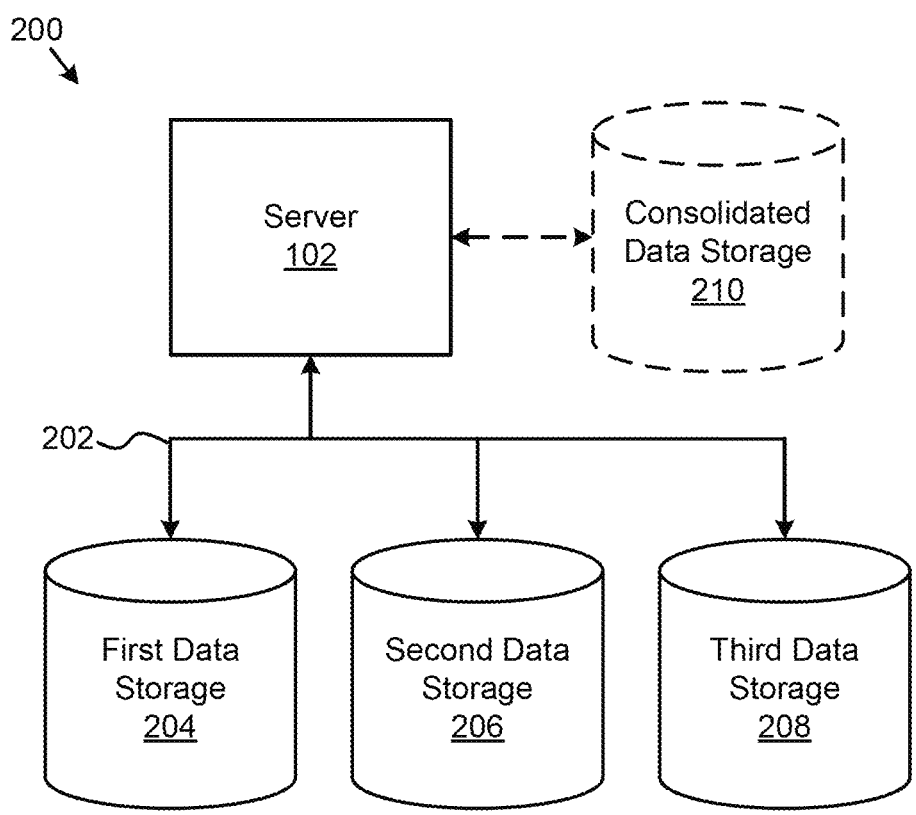
FIG. 2 is a schematic block diagram illustrating one embodiment of a database system for rapid assessment of lab value distributions.

FIG. 2 illustrates one embodiment of a data management system 200 configured to store and manage data for rapid assessment of lab value distributions. In one embodiment, the system 200 may include a server 102. The server 102 may be coupled to a data-bus 202. In one embodiment, the system 200 may also include a first data storage device 204, a second data storage device 206 and/or a third data storage device 208. In further embodiments, the system 200 may include additional data storage devices (not shown). In such an embodiment, each data storage device 204-208 may host a separate database of healthcare claim data, lab data, physical test data, disease progression data, demographic data, socioeconomic data, administrative data, clinical data, or the like. The customer information in each database may be keyed to a common field or identifier, such as an individual's name, social security number, customer number, or the like. Alternatively, the storage devices 204-208 may be arranged in a RAID configuration for storing redundant copies of the database or databases through either synchronous or asynchronous redundancy updates.

In one embodiment, the server 102 may submit a query to selected data storage devices 204-208 to collect a consolidated set of data elements associated with an individual or group of individuals. The server 102 may store the consolidated data set in a consolidated data storage device 210. In such an embodiment, the server 102 may refer back to the consolidated data storage device 210 to obtain a set of data elements associated with a specified individual or group. Alternatively, the server 102 may query each of the data storage devices 204-208 independently or in a distributed query to obtain the set of data elements associated with a specified individual or group. In another alternative embodiment, multiple databases may be stored on a single consolidated data storage device 210.

In various embodiments, the server 102 may communicate with the data storage devices 204-210 over the data-bus 202. The data-bus 202 may comprise a SAN, a LAN, or the like. The communication infrastructure may include Ethernet, Fibre-Chanel Arbitrated Loop (FC-AL), Small Computer System Interface (SCSI), and/or other similar data communication schemes associated with data storage and communication. For example, there server 102 may communicate indirectly with the data storage devices 204-210; the server may first communicate with a storage server or storage controller 106.

In one example of the system 200, the first data storage device 204 may store data associated with clinical data that may be comprised in insurance claims made by one or more individuals. The clinical data may include data associated with medical services, procedures, and prescriptions utilized by the individual. In one embodiment, the second data storage device 206 may store diagnosis data associated with the individual. The diagnosis data may include one or more diagnoses of conditions which the individual suffers from or is at risk of. The third data storage device 208 may store lab test data associated with the individual. For example, the third data storage device 208 may include data associated with the individual's lab test results and/or clinical observations. A fourth data storage device (not shown) may store demographic data. For example, the demographic data may include information relating to the individual's demographics include gender, race or ethnicity, age, income, disabilities, mobility, educational attainment, home ownership, employment status, location, or the like.

The server 102 may host a software application configured for rapid assessment of lab value distributions. The software application may further include modules for interfacing with the data storage devices 204-210, interfacing a network 108, interfacing with a user, and the like. In a further embodiment, the server 102 may host an engine, application plug-in, or application programming interface (API). In another embodiment, the server 102 may host a web service or web accessible software application.

Figure 3:
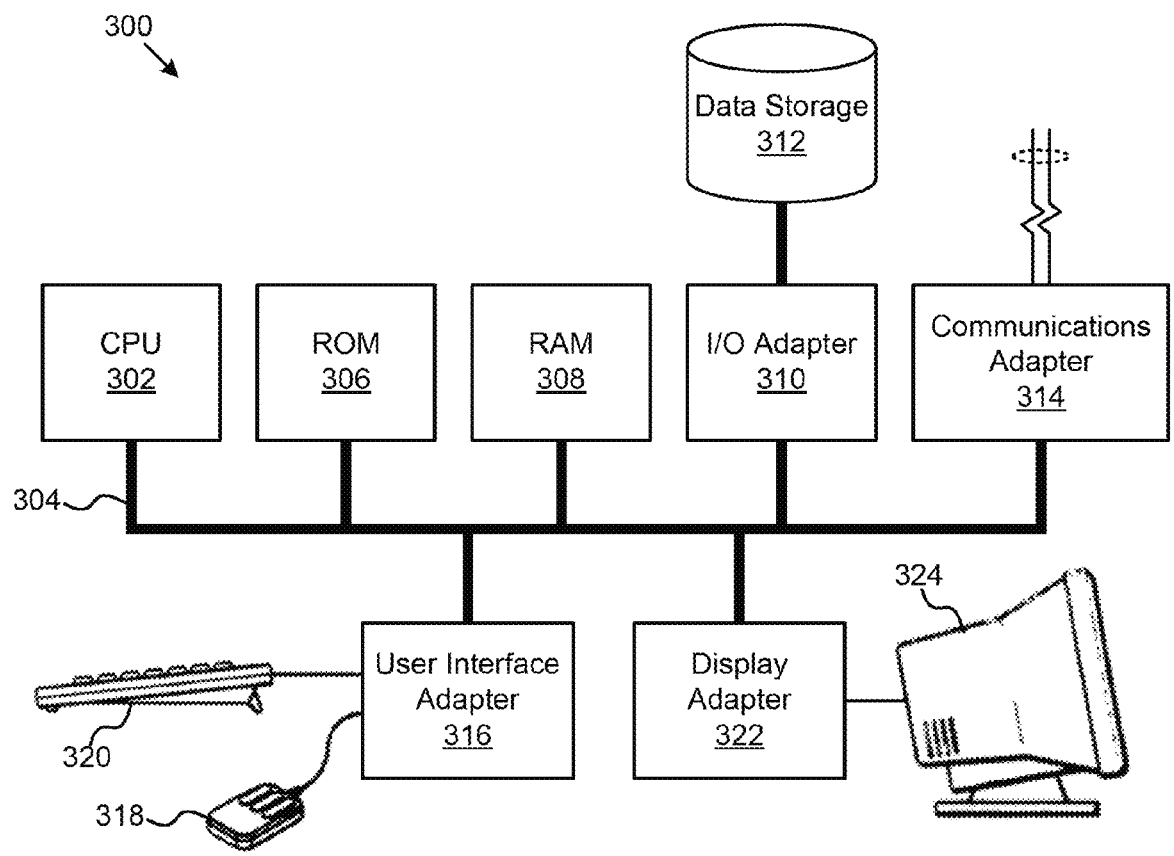
FIG. 3 is a schematic block diagram illustrating one embodiment of a computer system that may be used in accordance with certain embodiments of the system for rapid assessment of lab value distributions.

FIG. 3 illustrates a computer system 300 adapted according to certain embodiments of the server 102 and/or the user interface device 110. The central processing unit (CPU) 302 is coupled to the system bus 304. The CPU 302 may be a general purpose CPU, a processor, or a microprocessor. The present embodiments are not restricted by the architecture of the CPU 302, so long as the CPU 302 supports the modules and operations as described herein. The CPU 302 may execute the various logical instructions according to the present embodiments. For example, the CPU 302 may execute machine-level instructions according to the exemplary operations described below with reference to FIGS. 7-9.

The computer system 300 also may include Random Access Memory (RAM) 308, which may be SRAM, DRAM, SDRAM, or the like. The computer system 300 may utilize RAM 308 to store the various data structures used by a software application suitably programmed for rapid assessment of lab value distributions. The computer system 300 may also include Read Only Memory (ROM) 306 which may be PROM, EPROM, EEPROM, optical storage, or the like. The ROM may store configuration information for booting the computer system 300. The RAM 308 and the ROM 306 hold user and system 100 data.

The computer system 300 may also include an input/output (I/O) adapter 310, a communications adapter 314, a user interface adapter 316, and a display adapter 322. The I/O adapter 310 and/or the user interface adapter 316 may, in certain embodiments, enable a user to interact with the computer system 300 in order to input information for authenticating a user, identifying an individual or group, receiving health profile information, or entering information like a medical code, a test code, a temporal range, a percentile, a limiting criterion, or a selected test value range. In a further embodiment, the display adapter 322 may display a graphical user interface associated with a software or web-based application for generating an output comprising a distribution graph.

The I/O adapter 310 may connect to one or more storage devices 312, such as one or more of a hard drive, a Compact Disk (CD) drive, a floppy disk drive, a tape drive, to the computer system 300. The communications adapter 314 may be adapted to couple the computer system 300 to the network 106, which may be one or more of a LAN and/or WAN, and/or the Internet. The user interface adapter 316 may couple user input devices, such as a keyboard 320 and a pointing device 318, to the computer system 300. The display adapter 322 may be driven by the CPU 302 to control the display on the display device 324.

The present embodiments are not limited to the architecture of system 300. Rather the computer system 300 is provided as an example of one type of computing device that may be adapted to perform the functions of a server 102 and/or the user interface device 110. For example, any suitable processor-based device may be utilized including without limitation, including personal data assistants (PDAs), computer game consoles, and multi-processor servers. Moreover, the present embodiments may be implemented on application specific integrated circuits (ASIC) or very large scale integrated (VLSI) circuits. In fact, persons of ordinary skill in the art may utilize any number of suitable structures capable of executing logical operations according to the described embodiments.

Figure 4:
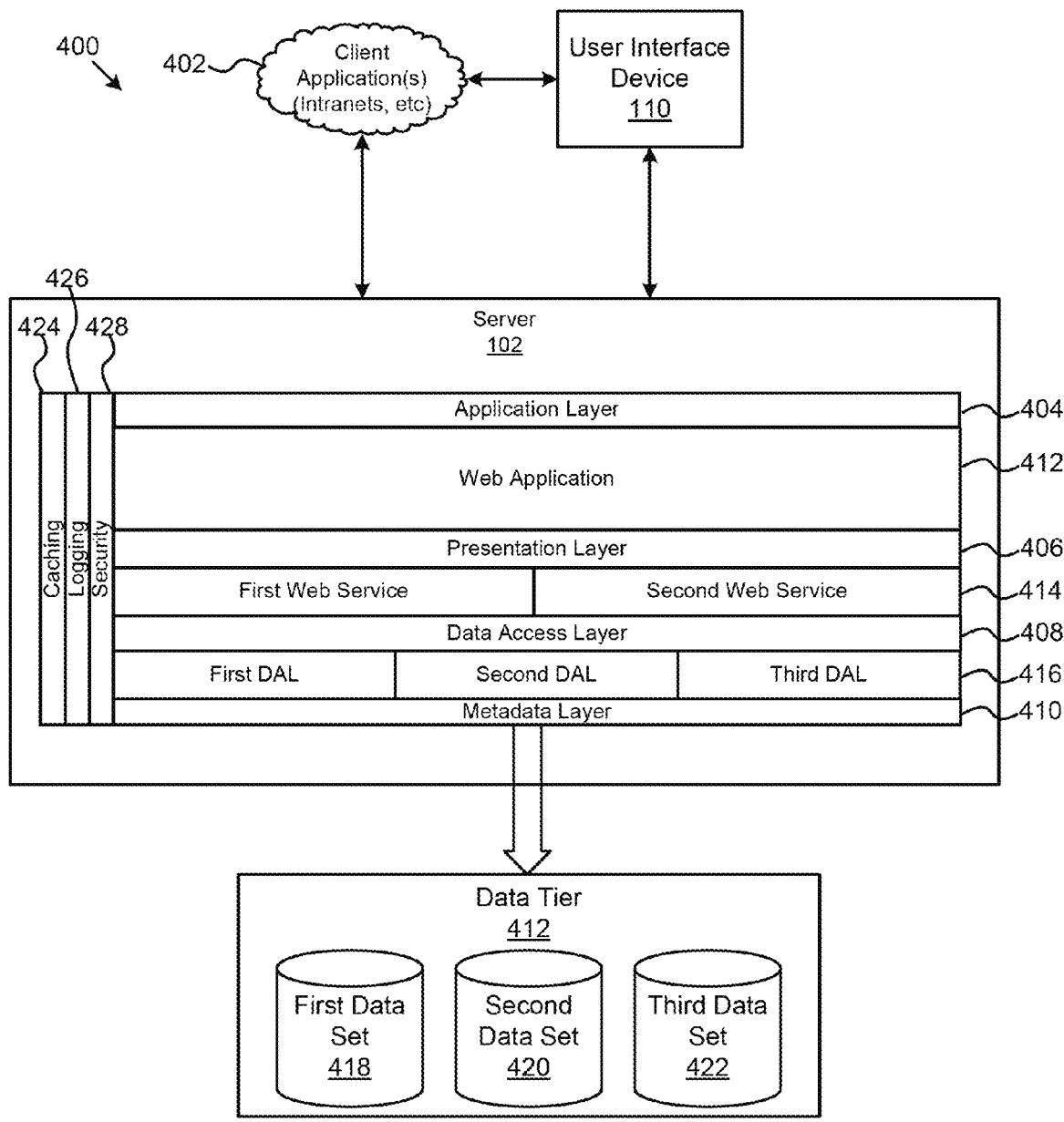
FIG. 4 is a schematic logical diagram illustrating one embodiment of abstraction layers of operation in a system for rapid assessment of lab value distributions.

FIG. 4 illustrates one embodiment of a network-based system 400 for rapid assessment of lab value distributions. In one embodiment, the network-based system 400 includes a server 102. Additionally, the network-based system 400 may include a user interface device 110. In still a further embodiment, the network-based system 400 may include one or more network-based client applications 402 configured to be operated over a network 108 including an intranet, the Internet, or the like. In still another embodiment, the network-based system 400 may include one or more data storage devices 104.

The network-based system 400 may include components or devices configured to operate in various network layers. For example, the server 102 may include modules configured to work within an application layer 404, a presentation layer 406, a data access layer 408 and a metadata layer 410. In a further embodiment, the server 102 may access one or more data sets 418-422 that comprise a data layer or data tier 412. For example, a first data set 418, a second data set 420 and a third data set 422 may comprise a data tier 412 that is stored on one or more data storage devices 204-208.

One or more web applications 412 may operate in the application layer 404. For example, a user may interact with the web application 412 though one or more I/O interfaces 318 and 320 configured to interface with the web application 412 through an I/O adapter 310 that operates on the application layer. In one particular embodiment, a web application 412 may be provided for rapid assessment of lab value distributions that includes software modules configured to perform the steps of receiving a medical code, searching a database stored on a data storage device to obtain a first group of records associated with individuals having the medical code, wherein each record of the first group of records is identified by a test code, searching the database to obtain a second group of records associated with a control population, wherein each record of the second group of records is identified by the test code, and generating an output comprising a distribution graph on a shared scale from the first and second group of records.

In a further embodiment, the server 102 may include components, devices, hardware modules, or software modules configured to operate in the presentation layer 406 to support one or more web services 414. For example, a web application 412 may access or provide access to a web service 414 to perform one or more web-based functions for the web application 412. In one embodiment, a web application 412 may operate on a first server 102 and access one or more web services 414 hosted on a second server (not shown) during operation.

For example, a web application 412 for identifying diagnostic records and/or analyzing diagnostic data, or other information may access a first web service 414 for identifying records of a first group of individuals associated with a diagnostic code and a second web service 414 for identifying a control population such as a normal group or a cohort group. The web services 414 may receive a medical code. In response, the web service 414 may return data associated with individuals having the medical code, statistics, distributions, graphs, or the like. One of ordinary skill in the art will recognize various web-based architectures employing web services 414 for modular operation of a web application 412.

In one embodiment, a web application 412 or a web service 414 may access one or more of the data sets 418-422 through the data access layer 408. In certain embodiments, the data access layer 408 may be divided into one or more independent data access layers (DALs) 416 for accessing individual data sets 418-422 in the data tier 412. These individual data access layers 416 may be referred to as data sockets or adapters. The data access layers 416 may utilize metadata from the metadata layer 410 to provide the web application 412 or the web service 414 with specific access to the data set 412.

For example, the data access layer 416 may include operations for performing a query of the data sets 418-422 to retrieve specific information for the web application 412 or the web service 414. In a more specific example, the data access layer 416 may include a query for records associated with individuals who have been diagnosed with a particular disease, such as diabetes, or who are associated with a medical code (where lab values may include a range of interest), such as an ICD-9 code, associated with a diagnosis of diabetes.

Figure 5:
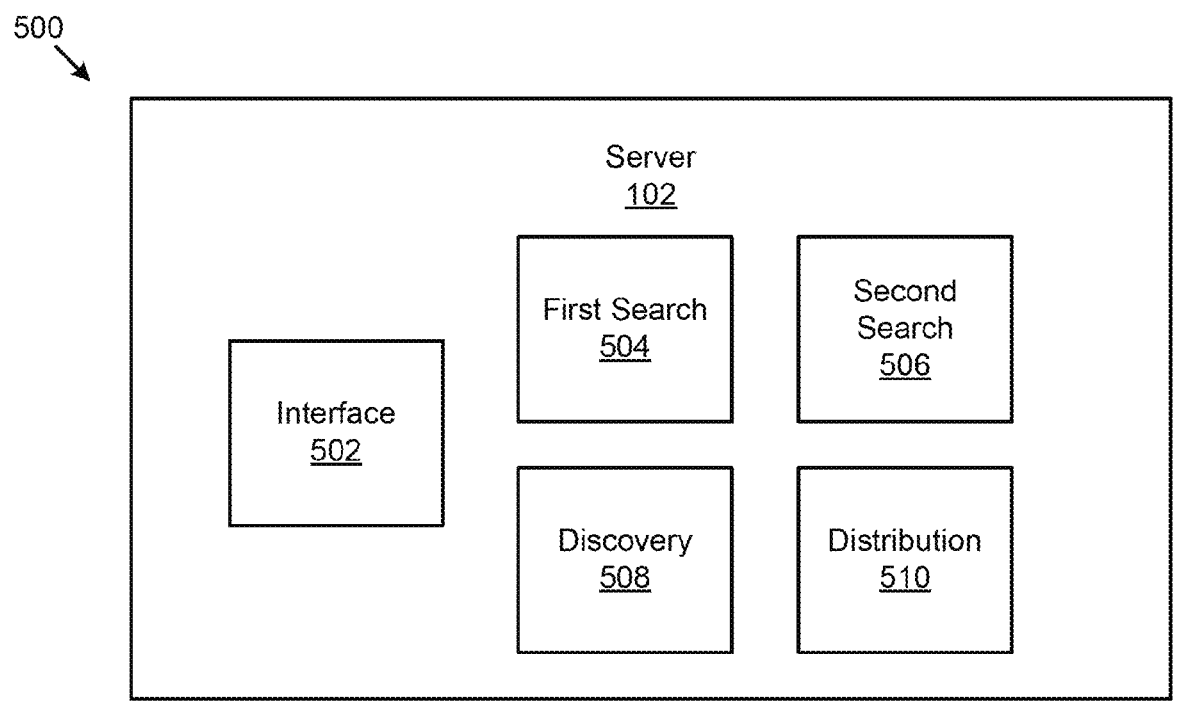
FIG. 5 is a schematic block diagram illustrating one embodiment of a system for rapid assessment of lab value distributions.

FIG. 5 illustrates a certain embodiment of a system 500 for rapidly processing and viewing lab value distributions. In one embodiment, the system 500 comprises a data storage device 104 and a server 102 configured to load and operate software modules 502-508 configured for rapid assessment of lab value distributions. Alternatively, the system 500 may include hardware modules 502-508 configured with analogue or digital logic, firmware executing FPGAs, or the like configured to receive a medical code, search a database stored on a data storage device to obtain a first group of records associated with individuals having the medical code, wherein each record of the first group is identified by a test code, search the database to obtain a second group of records associated with a control population, wherein each record of the second group is identified by the test code, and generate an output comprising a distribution graph on a shared scale from the first and second group of records. In such embodiments, the system 500 may also include an interface 502, such as an I/O adapter 310, a communication adapter 314, a user interface adapter 316, or the like.

In one embodiment, the server 102 may include one or more software defined modules configured to search a dataset 418-422 on a data storage device 204-208 to obtain a first group of records associated with individuals having the medical code, wherein each record of the first group is identified by a test code, search the database to obtain a second group of records associated with a control population, wherein each record of the second group is identified by the test code, and generate an output comprising a distribution graph on a shared scale from the first and second group of records. In one embodiment, these modules may include an interface module 502, a first search module 504, a second search module 506, and a distribution module 510. Optionally, the server 102 may also include a discovery module 508 as described in further detail below with relation to FIG. 6.

Generally, the interface module 502 may receive user inputs and display user outputs. For example, the interface module 502 may receive a medical code. The interface module may further receive one or more test codes, temporal interval, limiting criterion, percentile, selected test value ranges, and/or other user inputs. In a further embodiment, the interface module 502 may display discovery or detailed distribution analysis results. Such analysis results may include statistics, tables, charts, graphs, recommendations, and the like.

Structurally, the interface module 502 may include one or more of an I/O adapter 310, a communications adapter 314, a user interface adapter 316, and/or a display adapter 322. The interface module 502 may further include I/O ports, pins, pads, wires, busses, and the like for facilitating communications between the CPU 302 and the various adapters and interface components 310-324. The interface module may also include software defined components for interfacing with other software modules on the server 102.

In a specific embodiment, the server 102 may load and execute computer software configured to generate, retrieve, send, or otherwise operate SQL instructions. For example, the first search module 504 may communicate a first SQL query to the data storage device 104, which is configured to search the database for a first group of records associated with individuals having the medical code and identified by the test code.

The medical code may include a medical code used to group and identify diseases, disorders, symptoms, or medical signs and stored in a database of healthcare insurance information, a medical code indicative of a risk of developing a pathologic or disease condition, or a medical code identifying a treatment or a procedure. In a specific embodiment, the first search operation may identify a first group of individuals having records that include a specified ICD-9 medical code. For example, the first search may identify a first group of records in the database associated with individuals that have been diagnosed with diabetes. In another embodiment, the medical code may represent a risk, such as a metabolic syndrome, which is characterized by a group of metabolic risk factors or a combination of medical disorders that increase the risk of developing cardiovascular disease and diabetes. In a further embodiment, the medical code may include an identification or classification of individuals after treatment with one or more drugs or procedures for post-treatment or post-procedure diagnosis.

In an additional embodiment, the test code may be a code or classification for identifying a laboratory test or a clinical test or observation, such as a LOINC® code (Logical Observations Identifiers, Names, Codes), a universal code system for reporting laboratory and other clinical observations. For each observation, the database may include a code (of which 25 000 are laboratory test observations), a long formal name, a "short" 30-character name, and synonyms. It was identified by the Health Level Seven (HL7) Standards Development Organization as a preferred code set for laboratory test names in transactions between health care facilities, laboratories, laboratory testing devices, and public health authorities.

A record may comprise multiple lab test values identified by a common test code, wherein an average, first reading or last reading, or the like of the multiple values can be used to represent a data point for this record.

The first or second search may also involve a temporal component to aggregate records. If a test code has a time aspect, the searches may obtain multiple records associated with the same individual, but identified by a set of test codes at different time point within a common time interval. Those records may be processed, e.g., averaged, to yield a data value representing the time interval associated with the individual.

In certain aspects, the first search module 504 may be configured to search the database for a first group of records within a selected temporal interval, while matching the test code and medical code. Specifically, the first search module 504 may generate a first search query configured to retrieve for a first group of records within a selected temporal interval, while matching the test code and medical code. In a further embodiment, the first group of records may include a temporal component, which may specify a time period before, during, or after an event, such as a diagnosis, a disease or disorder or onset, a procedure, or a drug treatment. In a particular aspect, the first group of records may be from within a clean period or disease-free period before the individuals are diagnosed with a disease or a disorder, for example, from within about 30, 60, 120, or 180 days before a diabetic diagnosis.

The second search module 506 may generate and/or communicate a second SQL query to the database in response to or independent of the results of the first SQL query. The second query may be configured to search the database for a second group of records, each record in the second group of records identified with the same test code as that identify the records in the first group, but associated with a control population. The second group of records may be cohorts of the first group of records, or records of a normal group, or all records identified by the test code in the database, or records filtered by a limiting criterion which is shared by the first group of records. Such a limiting criterion may include a field value that indicates certain specified characteristics of the individuals associated with the records, such as age, gender, lab tests, lab results, other diseases or diagnoses, use of medication, and the like. In a certain embodiment, the second group of records may also have a temporal component or are associated with a temporal interval, for example, each record in the second group may be associated with individuals having at least three years of record in the database.

By way of example, the first search module 504 may identify a first group of individuals that have been diagnosed with diabetes or some other illness based on an ICD-9 medical code associated with such a medical diagnosis. The second search module 506 may then identify cohorts for each individual or record identified by the first search. The cohorts may share one or more common second index attributes with the individuals or records identified in the first group, such as age, gender, or the like; however, the cohorts would not have the medical code. In this example, the cohorts may be the same age and gender as the individuals in the first group, but not have been diagnosed with diabetes.

In another embodiment, the second search module 506 may generate a group of records associated with a normal group, such as a relatively normal group of individuals not associated with the medical code used in the first search or a normal group of disease-free individuals, a master group of records which include test values associated with each lab test and lab test unit stored in the database, or a group of filtered records associated with a selected limiting criterion, which can be created before, during or after the first search, or dynamically at run time applying any desired limiting criterion, such as age or gender.

In a further embodiment, the first search module 504 and the second search module 506 may be integrated into a single search module. Specifically, a single set of SQL instructions may be used to both identify the first group of records and identify the second group of records. The benefits of this embodiment may include reduced system overhead, reduced search and analysis time, reduced labor for configuration and generation of queries, etc. For example, with a single integrated SQL query, a user may be able to obtain results for analysis in far less time than the user might otherwise expect. Such an embodiment may not require separate analysis and generation of separate queries for the first group and the second group. Consequently, a significant time savings may be realized.

In one embodiment, the discovery module 508 may discover one or more lab tests relating to disease diagnosis or treatment evaluation. In order to do so, the discovery module 508 may extract the difference between representative values from the first and second group of records identified by the same test code but associated with different diagnosis status. For example, the discovery module may include analogue or digital logic, firmware, or software configured to carry out one or more discoveries according to one or more predefined logic functions. In a further embodiment, the server 102 may include a software defined discovery module 508 configured to perform analysis and comparison of the information and data retrieved from the database for the first group of records and the associated second group of records.

In a specific embodiment, the first search module 504 and the second search module 506 may feed retrieved data into a spreadsheet configured to perform one or more calculations on the data. For example an Excel® spreadsheet may include one or more embedded functions or operations configured to calculate statistics such as percentages, averages, odds ratios and other probabilities, counts, summations, and the like. The data may be automatically imported into a spreadsheet using a macro, a software-based script, or the like. In an alternative embodiment, the discovery module 508 may include hard-coded or dynamically variable software functions for calculating such statistics and generating results for a user. In a further embodiment, the discovery module 508 may also create outputs such as statistics, tables, charts, graphs, recommendations, and the like, and particularly identify one or more test codes that indicate a significant difference between two groups of records based on a selected discovery threshold or criterion. "Significant difference" may be referred to as a statistically significant difference, such as a significance level of 5%, 1% or 0.1%.

Figure 6:
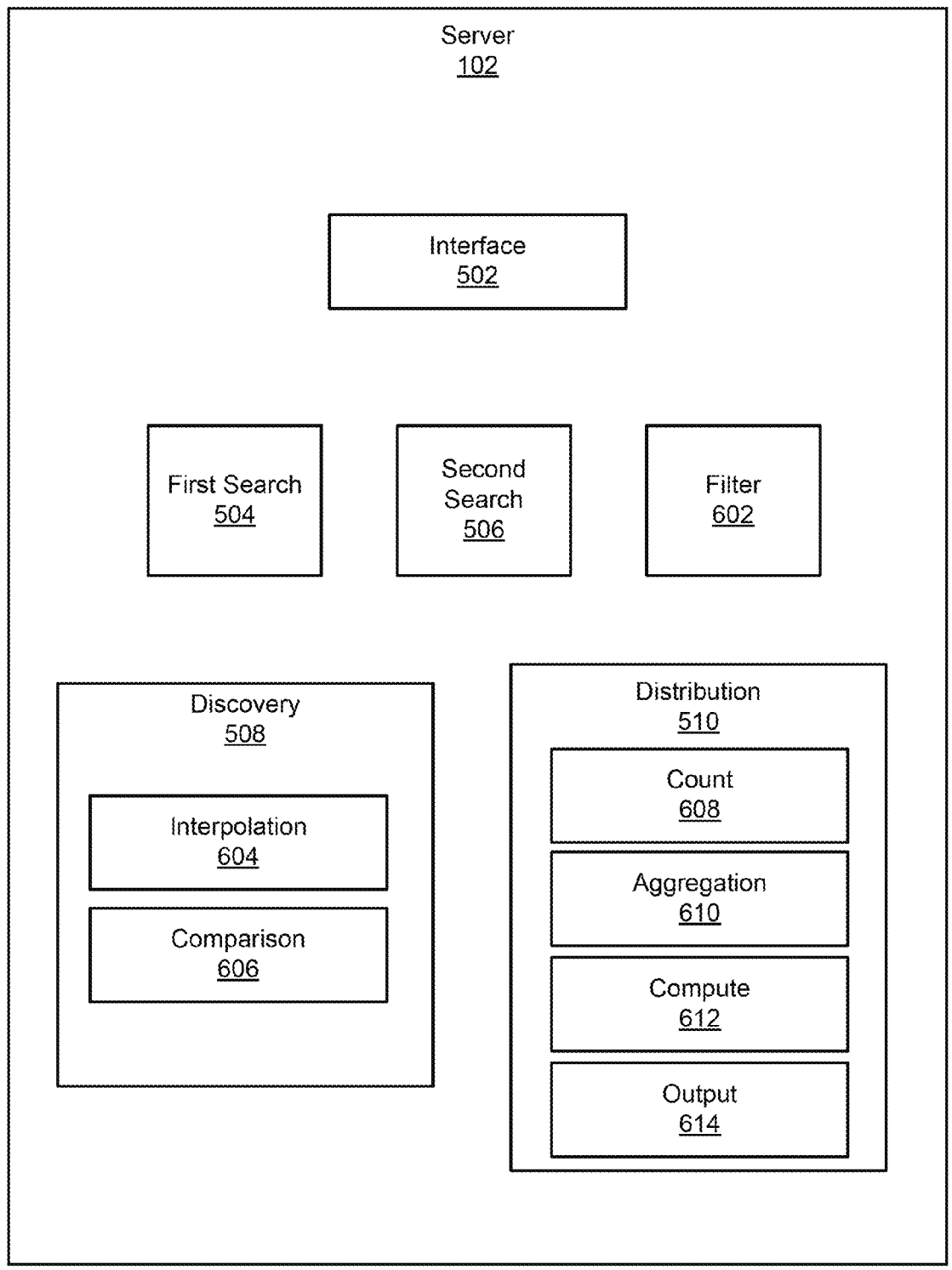
FIG. 6 is a schematic block diagram illustrating one embodiment of a system for rapid assessment of lab value distributions.

FIG. 6 illustrates a further embodiment of a system 500 for rapid assessment of lab value distributions. The system 500 may include a server 102 as described in FIG. 5. In a further embodiment, the server 102 may include additional software defined modules. For example, the server 102 may include a filter module 602. The discovery module 508 may further include an interpolation module 602 and a comparison module 604. The distribution module 510 may also include a count module 606, an aggregation module 608, a compute module 610, and a graph module 612.

In a further embodiment, the filter module 602 may narrow the first group or second group of records according to a limiting criterion. The filter module 602 may narrow the first or second group of records by restricting search parameters before the first or second search is performed. Alternatively, the filter module 602 may filter, remove, or otherwise delete the search results according to the limiting criterion. In a certain embodiment, multiple limiting criteria may be used to restrict the scope of the returned search results. In one embodiment, a limiting criterion may include a field value, such as record date, age, gender, or the like.

In an alternative embodiment, an SQL command generated by the server 102 or stored in RAM 308 or on the data storage device 312 may include instructions, that when executed by a storage controller 104 or the CPU 302 on the server 102, may perform a search for records matching the limiting criterion before or in combination with the first or second search. In a specific embodiment, an SQL operation embedded with the first or second search may activate the filter.

In a certain embodiment, the discovery module 508 may include an interpolation module 602 configured to derive a percentile value from the first group or the second group of records for comparison. The percentile may be any one ranging from 1% to 99%, such as a median, 5%, 32%, or 95%. The interpolation function may involve fitting a function to the data comprised in the records and evaluating that function at the desired point, or calculate the interpolated data by statistical methods. For example, interpolation methods may include a linear interpolation, a piecewise constant interpolation, a polynomial interpolation, a spline interpolation, or a non-linear interpolation such as an interpolation via Gaussian processes. In a specific embodiment, an SQL command may be generated by the serve 102 or the interpolation module 602 for calculating a percentile value from the first or second group of records. For example, such an SQL command may be designed similarly as that exemplified in FIG. 12 for linear interpolation from a group of data points.

In a further embodiment, the representative values of the corresponding percentile of both groups may be processed by a comparison module 604. For example, such a comparison module 604 may generate an output comprising a graph showing the difference between the two corresponding values, like a percentage shift of the first value associated with the medical code from the second value associated with a control group. For a particular medical code, a plurality of test codes may be assembled by the comparison module 604 to show the shift of the diagnosed group from the control group, as exemplified in FIG. 10. The relative degree of the shift associated with a test code may represent its relevance with the medical code and usefulness in the diagnosis.

In one embodiment, the distribution module 510 may include a count module 606 configured to count distinct records in the first group of records and the second group of records. The counting function may be implemented using a hardware-based counter. Alternatively, the counting function may be implemented in a software. In a specific embodiment, the server 102 or CPU 302 may execute SQL instructions configured to provide the record count in response to search or query results. In such an embodiment, the counting function may be integrated with the search and filter instructions into a single set of SQL commands or instructions.

In a further embodiment, the distribution module 510 may include an aggregation module 608 configured to aggregate records from the first group and from the second group according to a selected attribute, such as a series of bucket ranges created manually or derived empirically. The server 102 may also include other modules for computing, formatting, and otherwise producing statistics, including a compute module 610 and an output module 612. The compute module 610 may compute a probability in response to a ratio of a number of records in the first group having the selected attribute and a number of records in the second group having the selected attribute. The output module 612 may generate, format, and provide a graphical representation of the statistics. These modules 606-612 may be stand-alone modules implemented in hardware, firmware, or software. Alternatively, the functions may be accomplished through commercial calculation products or spreadsheets, software or SQL instructions that are integrated with the other functions of the server 102. In a specific embodiment, the distribution module 510, including some or all of its component modules 606-612, may communicate the statistics with the interface module 502 for display or communication to a user.

Although the various functions of the server 102 and the CPU or processor 302 are described in the context of modules, the methods, processes, and software described herein are not limited to a modular structure. Rather, some or all of the functions described in relation to the modules of FIGS. 5-6 may be implemented in various formats including, but not limited to, a single set of integrated instructions, commands, code, queries, etc. In one embodiment, the functions may be implemented in database query instructions, including SQL, PLSQL, or the like. Alternatively, the functions may be implemented in software coded in C, C++, C#, php, Java, or the like. In still another embodiment, the functions may be implemented in web based instructions, including HTML, XML, etc.

The schematic flow chart diagrams that follow are generally set forth as logical flow chart diagrams. As such, the depicted order and labeled steps are indicative of one embodiment of the presented method. Other steps and methods may be conceived that are equivalent in function, logic, or effect to one or more steps, or portions thereof, of the illustrated method. Additionally, the format and symbols employed are provided to explain the logical steps of the method and are understood not to limit the scope of the method. Although various arrow types and line types may be employed in the flow chart diagrams, they are understood not to limit the scope of the corresponding method. Indeed, some arrows or other connectors may be used to indicate only the logical flow of the method. For instance, an arrow may indicate a waiting or monitoring period of unspecified duration between enumerated steps of the depicted method. Additionally, the order in which a particular method occurs may or may not strictly adhere to the order of the corresponding steps shown.

Figure 7:
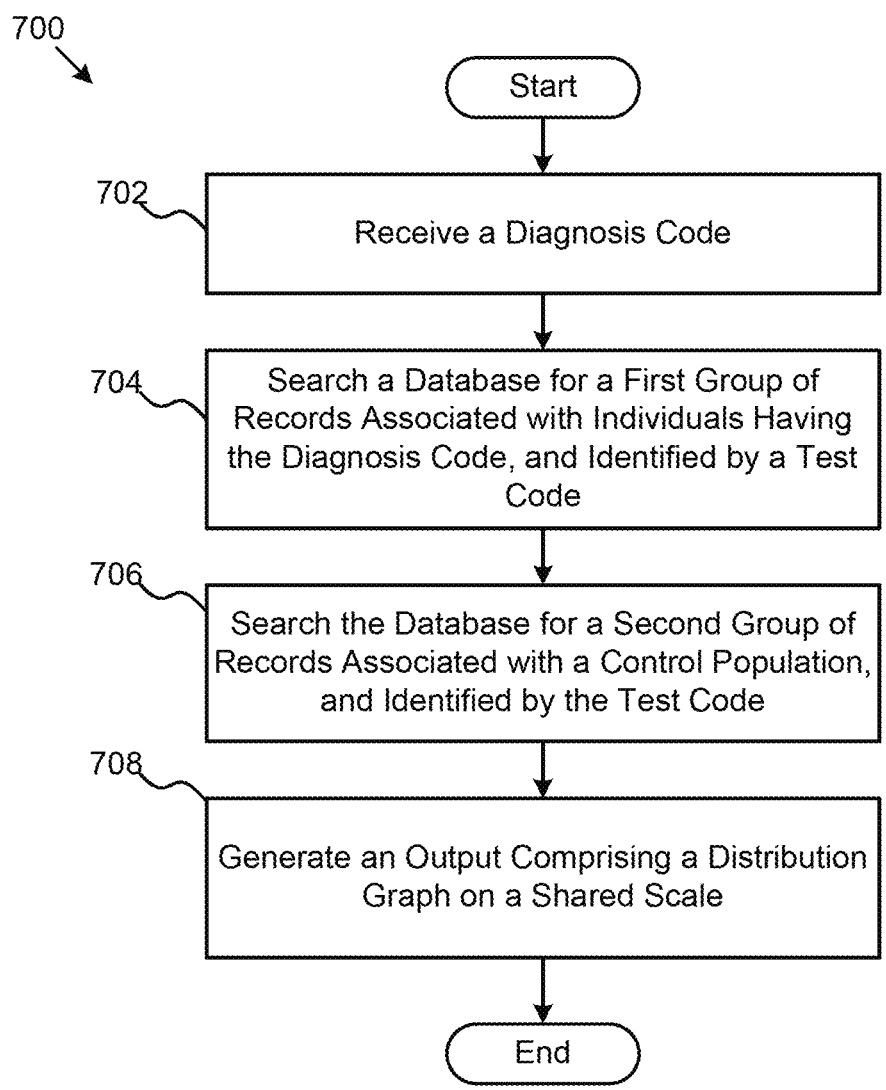
FIG. 7 is a schematic flowchart diagram illustrating one embodiment of a method for rapid assessment of lab value distributions.

FIG. 7 illustrates one embodiment of a method 700 for rapid assessment of lab value distributions. In one embodiment, the method 700 starts when the interface module 502 receives 702 a medical code. The medical code is also known as a diagnosis code or a clinical attribute of interest. The method 700 may continue when the server 102 issues a command to search 704 a database stored on the data storage device 104 for a first group of records. The first group of records may be associated with the individuals having the medical code, and identified by a test code. For example, the server 102 may send an SQL query to the database to retrieve healthcare records associated with individuals that have been diagnosed with diabetes as indicated by the presence of an ICD-9 code associated with diagnosis of diabetes in the individual's records, while also storing information about lab test values identified by one or more test codes.

The server 102 may then issue a command to search 706 the database for a second group of records. Each record in the second group of records may share a common test code with a record in the first group of records, but is associated with a control population, a majority of which does not have the medical code. For example, SQL query issued by the server 102 may also include a query statement to search for a second group of individuals, each individual having the same age and/or gender as an individual identified in the first group, but not having the diabetes medical code in their record. These individuals in the second group may be considered cohorts of the individuals in the first group of records. In another embodiment, the second group of records may be associated with a normal group which may include all health or disease-free individuals or a group including all individuals with records available in the database of all time points or a specific time period.

The server 102 may then receive the results from the database searches 704 and 706. The distribution module 510 may then generate 708 an output comprising a distribution graph on a shared scale from the first group of records and the second group of records. For example, a spreadsheet program may calculate distribution of records identified by the test code in the presence of the received medical code as compared with those of a control group. The distribution may include averages, probabilities, and other computational products including identification of trends and commonalities among the records.

Figure 8:
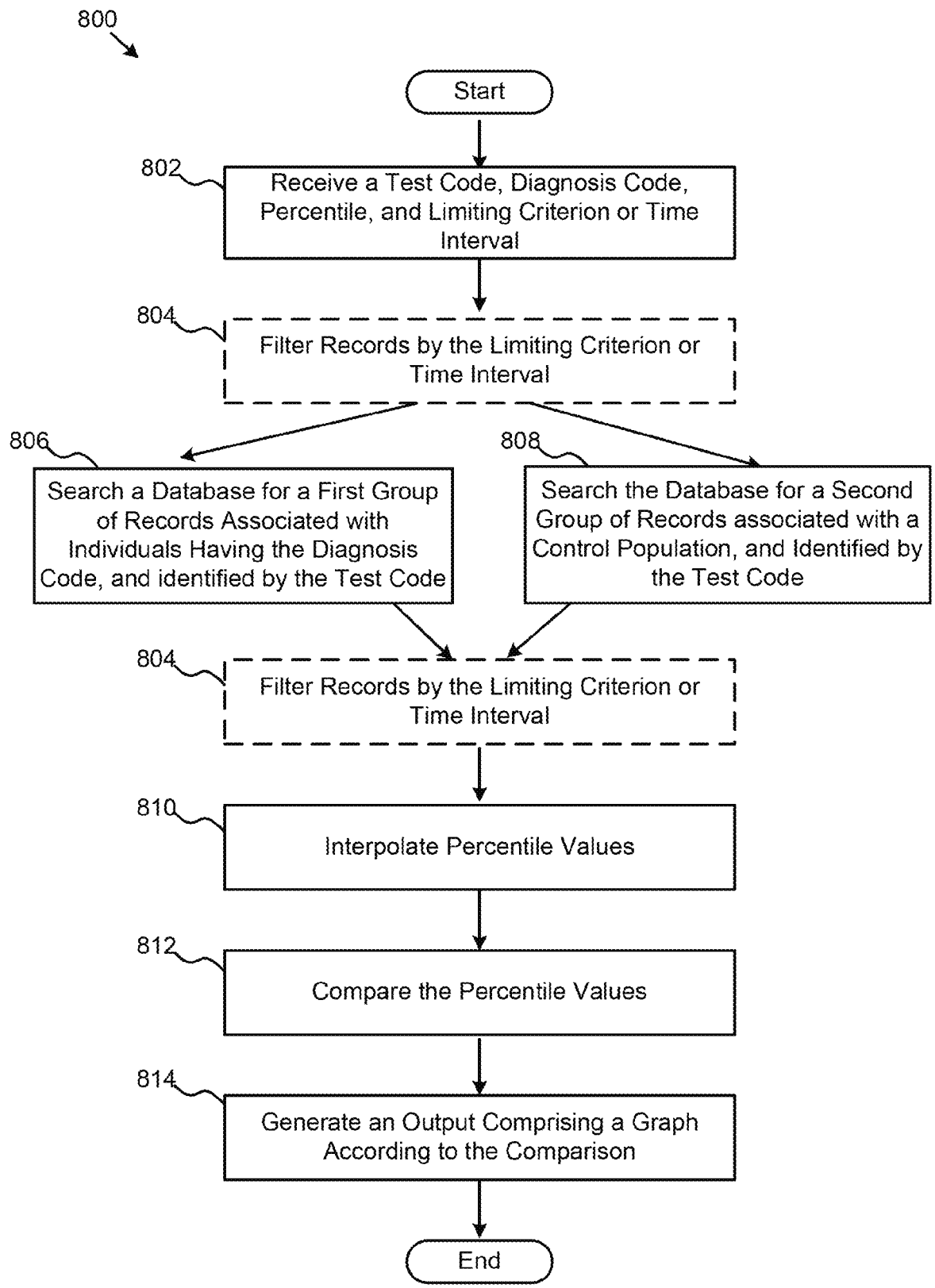
FIG. 8 is a schematic flowchart diagram illustrating one embodiment of a method for rapid assessment of lab value distributions.
Figure 9:
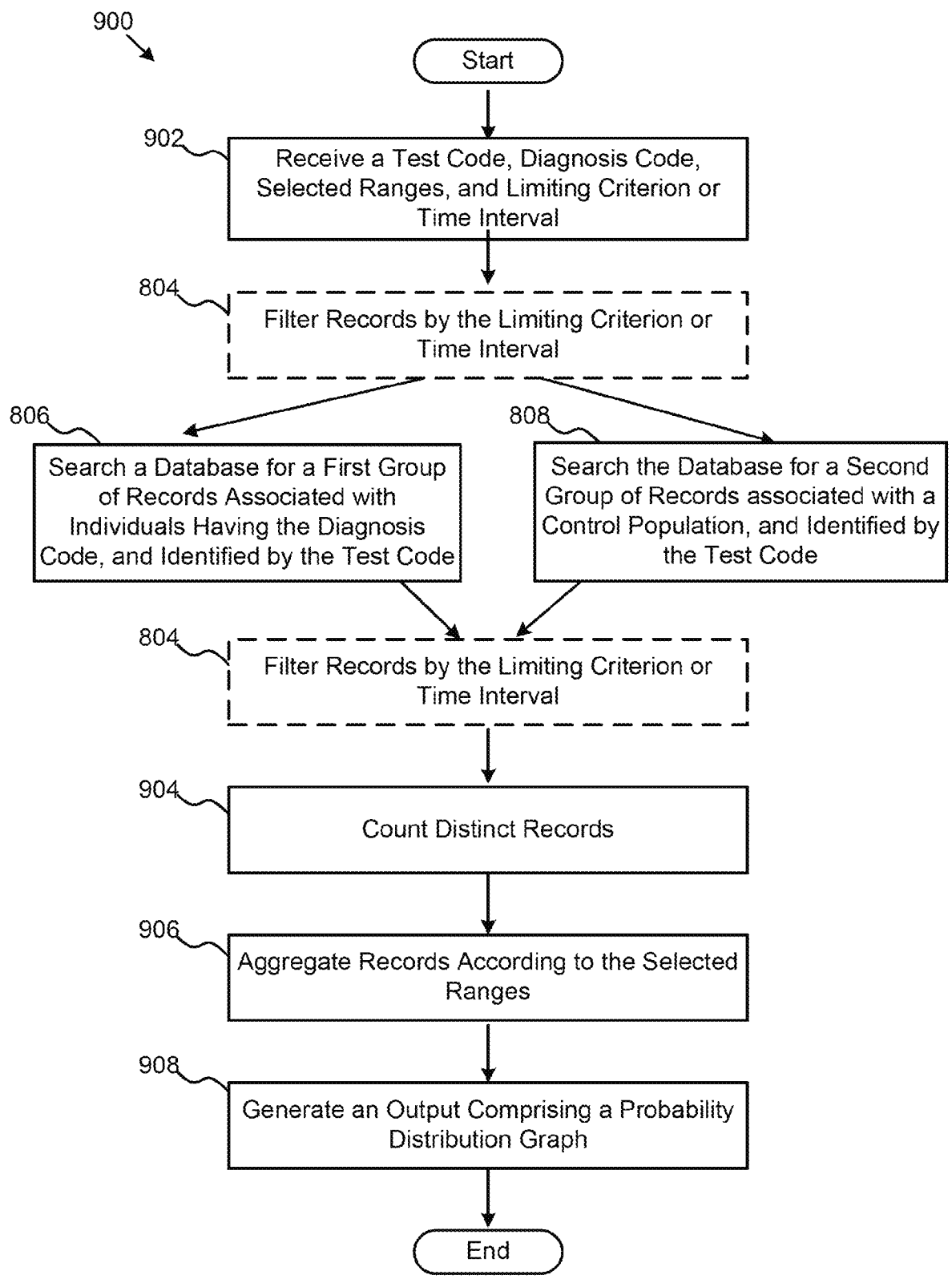
FIG. 9 is a schematic flowchart diagram illustrating one embodiment of a method for rapid assessment of lab value distributions.

FIG. 8 illustrates another embodiment of a method 800 for rapid assessment of lab value distributions. In one embodiment, the method 800 starts when the interface module 502 receives 802 a test code, a medical code, a percentile, and one or more limiting criteria or time intervals. For example, the interface module 502 may include a graphical user interface. The interface module 502 may receive user inputs consisting of identifiers or indicants of the test codes, medical codes, or limiting criteria. Such indicants may include a selection of a field value, such as an ICD-9 code value, an age value, a gender value, or the like.

Limiting criteria may include windowing values configured to limit or restrict the time frames from which records will be searched, restrictions on minimum enrollment time, minimum number of records, gender restrictions, age restrictions, weight restrictions, physical conditions, healthcare patterns, other diagnoses or identified lab values, and other similar threshold and limiting values. The filter module 602 may incorporate the limiting criterion into a query used to filter 802 the records by the limiting criterion before, during or after the search 806 or the search 808. For example, the query may search for all records associated with individuals that have been diagnosed with diabetes, but the query may be restricted to return only results associated with individuals that have at least two years worth of records in the database. In a further embodiment, the filter module 602 may use the same limiting criterion for both searches 806-808 to identify a cohort for the first group of records. Specific time interval relative to the diagnosis associated with the medical code may be also used to filter 804 records to assess lab value distributions at the specific time interval.

Figure 12:
FIG. 12 is an example of linear interpolation which may be used for rapid assessment of lab value distributions.

For the discovery module 508, the interpolation module 602 may interpolate 810 percentile values from both group of records according to a received or selected percentile. An example of interpolation 810 is illustrated in FIG. 12. The price records in FIG. 12 may be replaced by health care records. The server may send such an SQL instruction based on FIG. 12 to interpolate different percentile values of the records as exemplified in FIG. 10 for records in the presence of a plurality of test codes (e.g., LOINC code) listed in the first column in the presence of a common medical code, 292.4 representing thalassemia. In a further embodiment, the comparison module 604 may compare 812 the corresponding percentile values of both groups and generate 814 an output comprising a graph showing the comparison, such as a percentage shift of the median of the first group in the presence of thalassemia from the median of the second group associated with a normal population for multiple LOINC codes in FIG. 10. Discovery 810-814 may help identify or confirm test codes that may be potentially relevant for a particular medical code and may be used for disease diagnosis or prediction, as well as treatment evaluation. However, discovery steps of those test codes may be optional; for example, these steps may not be necessary for test codes known to be associated with the medical code.

Figure 11:
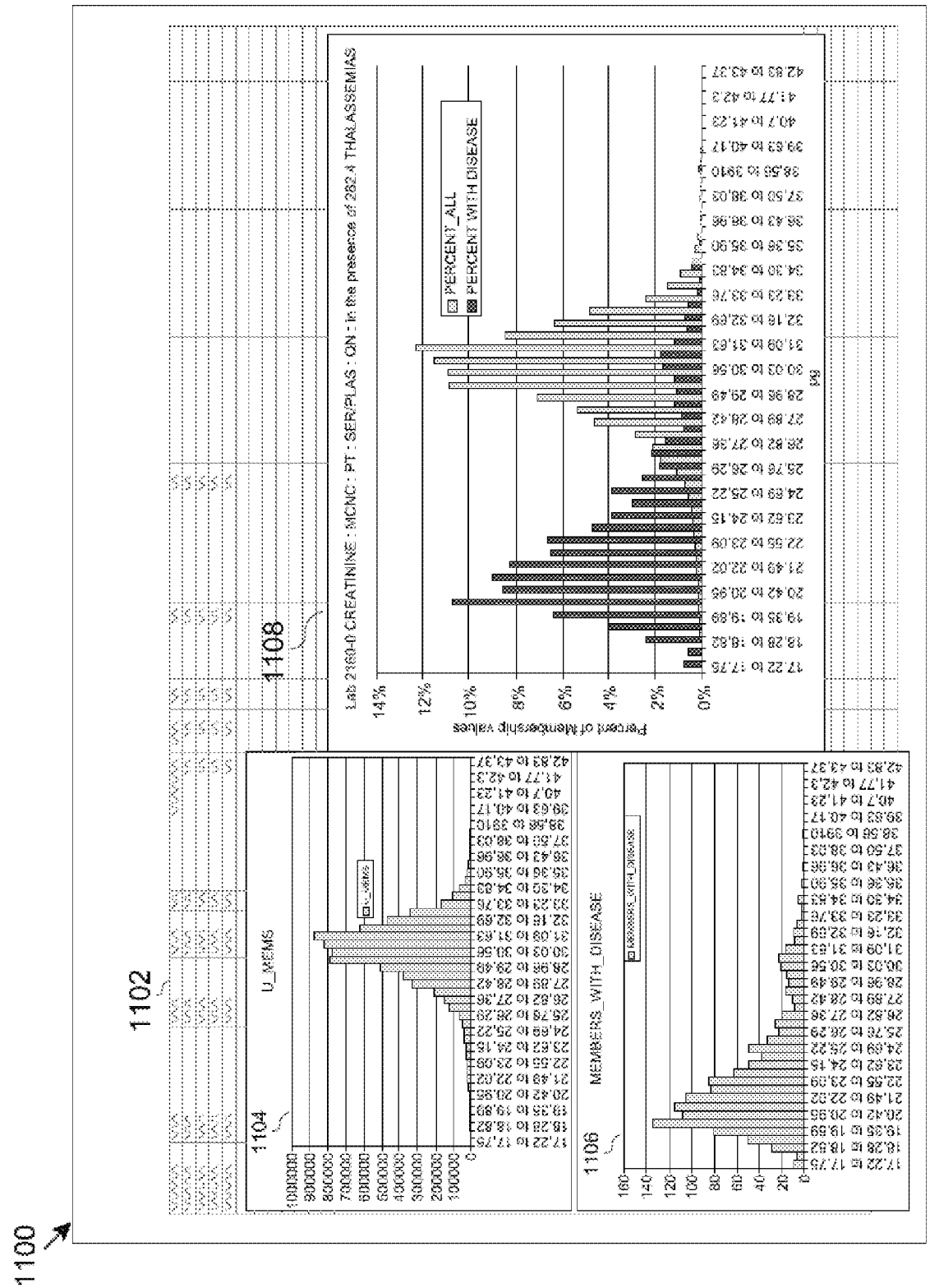
FIG. 11 is an output illustrating one embodiment of distribution results generated by rapid assessment of lab value distributions.

In the distribution module 510, records may also be retrieved by search 806 and 808, and optionally filter 804. In an embodiment, the count module 606 may count 904 distinct records in both groups for a total number of records and also records in each aggregated category as the aggregation module 608 may aggregate 906 records from the first group and from the second group according to a selected attribute, such as a series of bucketed ranges of test values for distribution. An example of aggregation 906 is illustrated in FIG. 11. The compute module 610 may then compute an odds ratio, an average, or some other mathematical statistic and the output module 612 may generate an output comprising one or more distribution graphs to display one or more statistics calculated by the server 102. For example, the graph may be a histogram as illustrated in FIG. 11.

In a specific example, the server 102 may send a single set of SQL instruction to perform the first search 806, perform the second search 808, and other searching functions, such as filtering 804.

In a further embodiment, the SQL instructions may include instructions for interpolating 810 percentile values from both groups. In a still further embodiment, the SQL instructions may also include comparing 812 the corresponding percentile values and generate 814 an output comprising a graph showing the comparison, for example, in the format of percentage shift which may also be ranked by the degree of shift. For example, one embodiment of SQL instructions that may be used to perform the method of FIG. 8 may include:

```
select c.loinc_code||' '||loinc_code_desc,a.*,b.*,-
(a.interpolated50th-
        b.interpolated50th)/(a.interpolated50th+b.interpolated50th)/
2 percent_shift_of_median from
foo_loinc_distribution_sigmas a,
loinc c,
(
select loinc_code,result_units_name,u_mem,max(case when .50
between decile and lead_decile then (lead_delta-
delta_from_index)/(lead_decile-decile)*0.50
        +(delta_from_index-(lead_delta-
delta_from_index)/(lead_decile-decile)*decile) else - 99999
end ) interpolated50th, max(case when .32 between decile and
lead_decile then (lead_delta-delta_from_index)/(lead_decile-
decile)*0.32 +(delta_from_index-(lead_delta-
        delta_from_index)/(lead_decile-decile)*decile) else -99999
end) interpolated32th, max(case when .95 between decile and
lead_decile then (lead_delta- delta_from_index)/(lead_decile-
decile)*0.95 +(delta_from_index-(lead_delta-
        delta_from_index)/(lead_decile-decile)*decile) else -99999
end ) interpolated95th,max(case when .05 between decile and
lead_decile then (lead_delta-delta_from_index)/(lead_decile-
decile)*0.05 +(delta_from_index-(lead_delta-
        delta_from_index)/(lead_decile-decile)*decile) else -99999
end ) interpolated5th, max(case when .68 between decile and
lead_decile then (lead_delta- delta_from_index)/(lead_decile-
decile)*0.68 +(delta_from_index-(lead_delta-
        delta_from_index)/(lead_decile-decile)*decile) else -99999
end ) interpolated68th
from
(
select iv4.*, cast(result_value_nbr as float)
delta_from_index,cast(rn as float)/u_mem decile,lead(cast(rn as
float)/u_mem) over (partition by loinc_code,result_units_name
        order by rn) lead_decile,lead(result_value_nbr) over
(partition by loinc_code, result_units_name order by rn)
lead_delta
from
(
select iv3.*, max(rn) over( partition by
loinc_code,result_units_name ) u_mem
from
(
select iv2.*, row_number( ) over ( partition by
loinc_code,result_units_name order by result_value_nbr asc) rn
from
(
select
a.loinc_code,a.result_units_name,a.individual_id,avg(result_value_
nbr) result_value_nbr
from
(
select individual_id,min(service_from_date) min_dos from
diagnosis a, foo_members_with_condition6 b where decm_code
like'250%' and b.dx=a.diagnosis_key group by individual_id
        ) iv,
foo_members_with_lab6 a
        where a.individual_id=iv.individual_id and service_from_date
between min_dos+−1400 and min_dos+−365
group by a.loinc_code,a.result_units_name,a.individual_id
) iv2
) iv3
) iv4 where u_mem>19
) iv5 group by loinc_code,result_units_name,u_mem
) b where a.loinc_code=b.loinc_code and
a.result_units_name=b.result_units_name and a.loinc_code not in
('0','1') and a.result_units_name <> ' '
```

-continued

```
and a.loinc_code=c.loinc_code and ( b.interpolated50th not between
a.interpolated32th and a.interpolated68th or
a.interpolated50th not between b.interpolated32th and
b.interpolated68th)
order by abs((a.interpolated50th-
b.interpolated50th)/(a.interpolated50th+b.interpolated50th)/2)
desc
```

In a further embodiment, the SQL instructions may include instructions for counting 904 distinct records and/or aggregating 906 the records. In still another embodiment, the same set of SQL instructions may include functions for generating 908 an output comprising a probability distribution graph by computing statistics, such as the odds ratio of a specified test value or range within the records. One particular embodiment of SQL instructions that may be used to perform the method of FIG. 9 may include:

```
select iv4.*,u_mems/totl percent_all,members_with_disease/tot2
percent_with_disease from (
select iv3.*,sum(u_mems) over ( ) totl,sum(members_with_disease)
over ( ) tot2 from (
select
b.loinc_code,b.result_units_name,rng,u_mems,rn,count(distinct
individual_id) members_with_disease from
(select * from foo_normal_distributions where loinc_code='785-6'
and result_units_name='pg' ) b
left outer join
(
select
a.individual_id,min_dos,decm_code,loinc_code,result_units_name,avg
(result_value_nbr) result_value_nbr from
(
SELECT decm_code, b.individual_id, MIN(service_from_date)
min_dos
FROM diagnosis a, foo_members_with_condition6 b
WHERE decm_code like '282.4'
AND b.dx=a.diagnosis_key
GROUP BY decm_code, b.individual_id
) iv2
,
foo_members_with_lab6 a
where a.individual_id=iv2.individual_id and service_from_date
between min_dos+−180 and min_dos+−2
group by
a.individual_id,min_dos,decm_code,loinc_code,result_units_name
) iv3 on ( iv3.loinc_code=b.loinc_code and
iv3.result_units_name=b.result_units_name and result_value_nbr
>bucketstart and result_value_nbr<= bucketend)
group by b.loinc_code,b.result_units name,rng,u_mems,rn
) iv3
) iv4 order by rn
```

Figure 10:
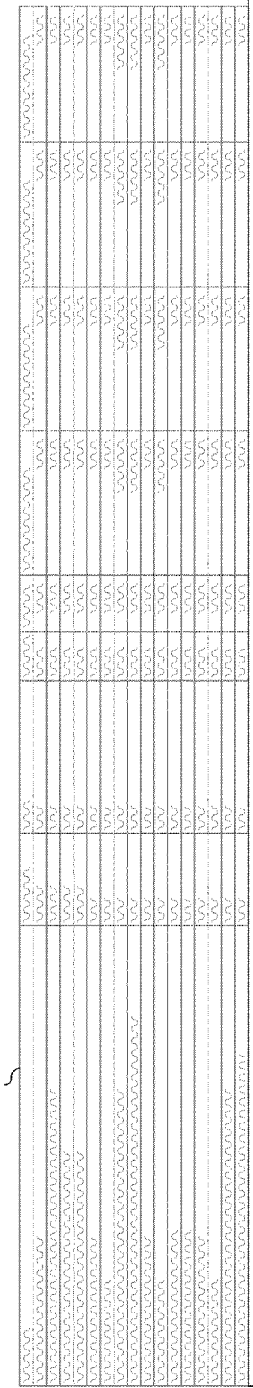
FIG. 10 is an output illustrating one embodiment of discovery results generated by rapid assessment of lab value distributions.
Figure 10:
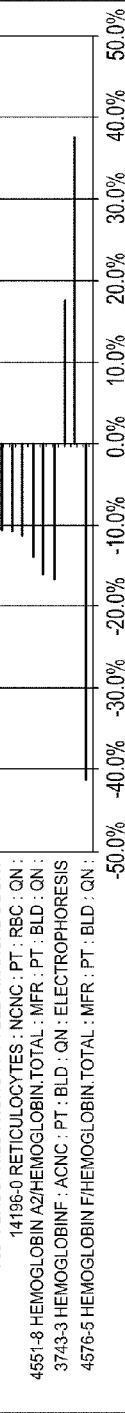

FIG. 10 illustrates one embodiment of an output 1000 from the discovery module 508, which may include an interpolation table 1002 or a comparison graph 1004. In a certain embodiment, each row in the table 1002 may represent a first group of records in the presence of a medical code 282.4 thalassemia that is identified by a specific test code in the first column. For example, the test code may be LOINC code 785-6 representing erythrocyte mean corpuscular hemoglobin, and the associated first group of records (not shown) may be interpolated to obtain values representing 50% (median), 32%, 95%, and 5%. In a particular embodiment, the median of the first group of records identified by the specific test code in the presence of the medical code is compared with the median of a control group of records, particularly, a normal group, which is the middle line corresponding to 0.0% in the graph 1004. The difference between the two medians for each test code is represented as a percentage shift (=(median of diseased group of records-median of normal group of records)/median of normal group of records×100%) from the middle line, which has also be used to rank the order of the list of test codes from least to most in terms of absolute value of difference.

FIG. 11 illustrates an embodiment of results or outputs that may be derived from the distribution module 510. A specific test code, for example, LOINC code 785-6, is received or selected for the first search 806 to identify a first group of records associated with the test code and in the presence of the medical code 282.4. A table 1102 may include one or more fields for displaying counting, aggregating and computing results. The first and second group of records may be aggregated according to selected attributes, in particular, a set of test value ranges (RNG field), and counted in each range with results presented in the U_MEM field for the second group (normal control) and in MEMBERS_WITH_DISEASE for the first group (diseased). Percentage of the number of records in each test value range over the total number of records in the first or second group may also be calculated to yield results shown in fields of PERCENT_DISEASED or PERCENT_ALL, respectively. Graph 1104 and 1106 show a distribution of numbers of records in the bucket ranges for normal group and diseased group, respectively. Histogram 1108 overlay the percentages of records in each value range for both groups and show a difference in their distribution pattern.

FIG. 12 illustrates an example for interpolation of a percentile value from a group of records. Protocol 1202 explains interpolating a raw source of random prices by using a linear function to extract a value at 80% by using SQL instructions. Table 1204 presents such a raw source of random prices and table 1206 shows the result of the interpolation of 80%.

Figure 13:
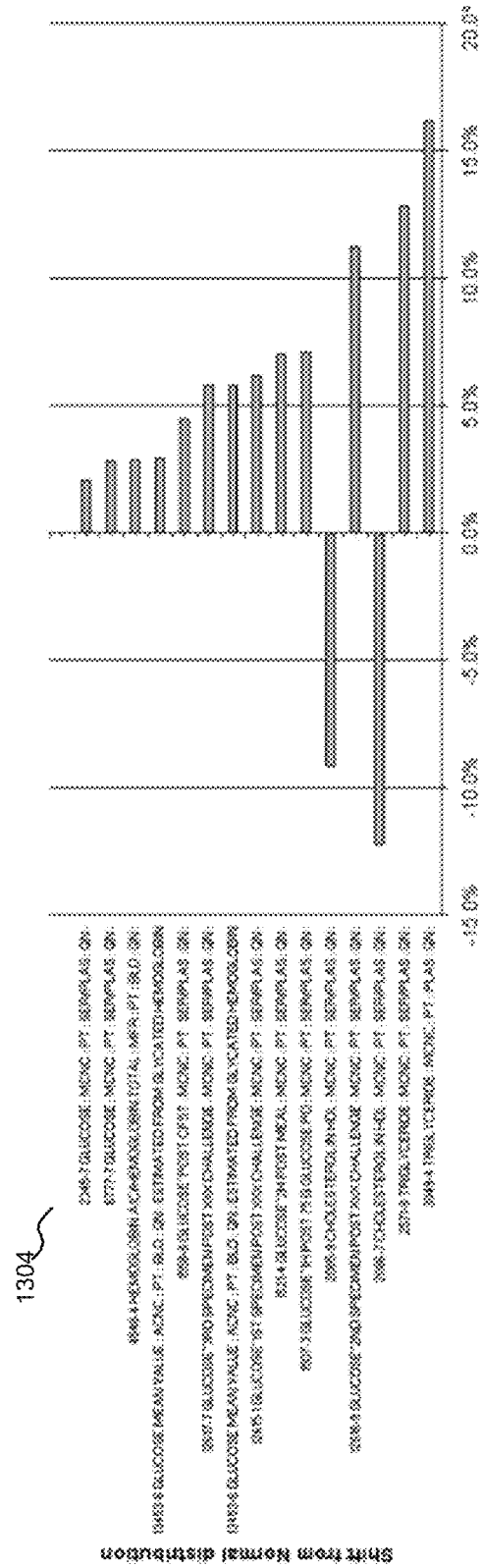
FIG. 13 is an output illustrating one embodiment of discovery results generated by rapid assessment of lab value distributions.

FIG. 13 illustrates an embodiment of the discovery module used for pre-disease diagnosis or predicting a risk for a disease. List 1302 provide examples of risk factors for identifying metabolic syndrome candidates, one or more of which may be used as the medical code to search for the first group of records in the database. Alternatively, a temporal window in combination with the diabetic medical code may be used to search a first group of records collected three years to thirty days prior to diabetic diagnosis or in the presence of a diabetic medical code. Graph 1304 shows the output comprising the ranked percentage shift of the medians of the first group of records from the normal medians for a plurality of test codes. A test code with a significant percentage shift may be a potential pre-diabetic marker or a useful diabetic early predictor, such as LOINC code 2086-7, associated with a nearly −12% shift.

Figure 14:
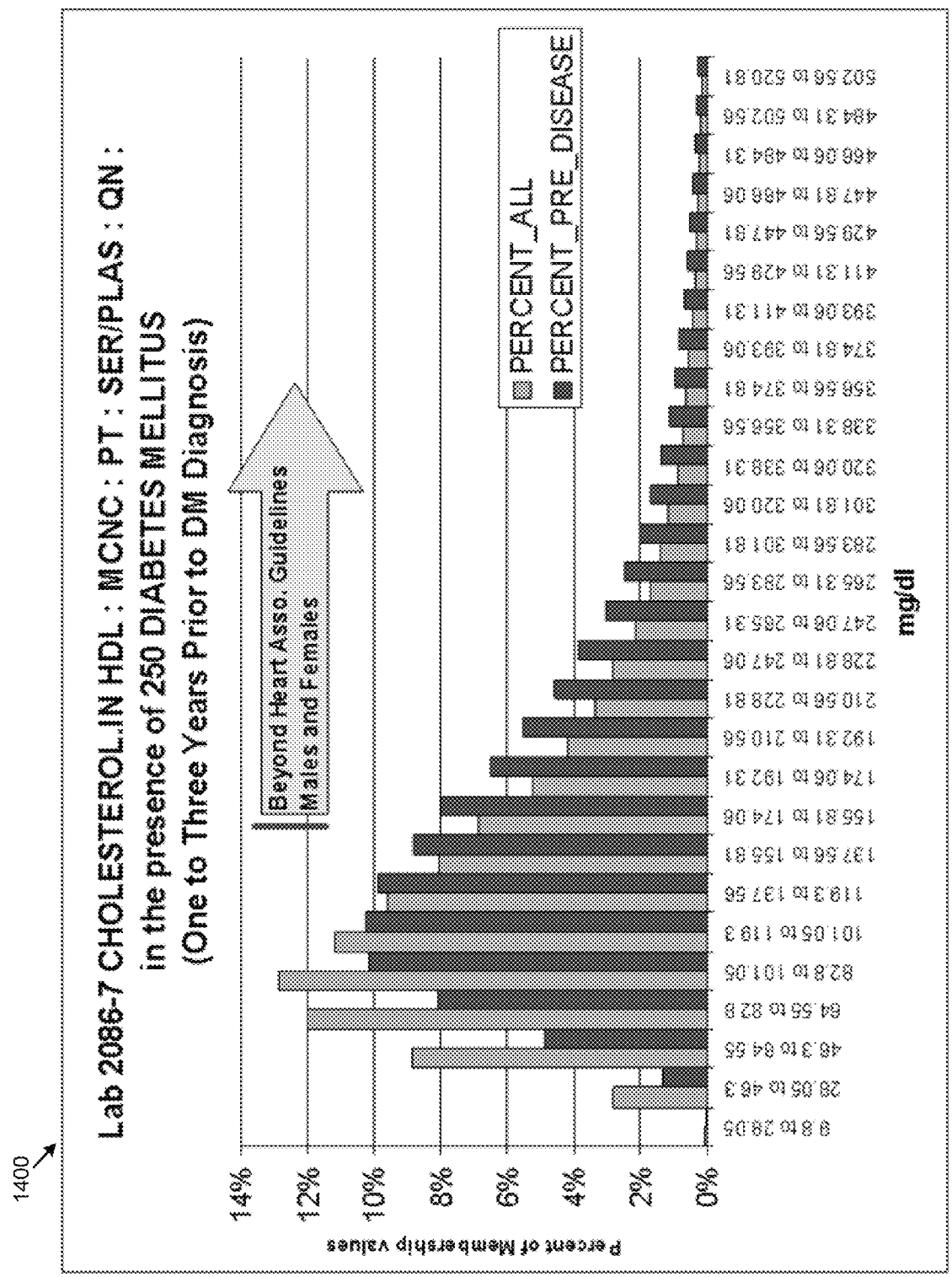
FIG. 14 is an output illustrating one embodiment of distribution results generated by rapid assessment of lab value distributions.

FIG. 14 illustrates an embodiment of the distribution module used for pre-disease diagnosis or predicting a risk for a disease. Distribution of percentage of records in each histogram range for the pre-disease group (one to three years prior to diabetes diagnosis) and control group are compared in graph 1400.

Figure 15:
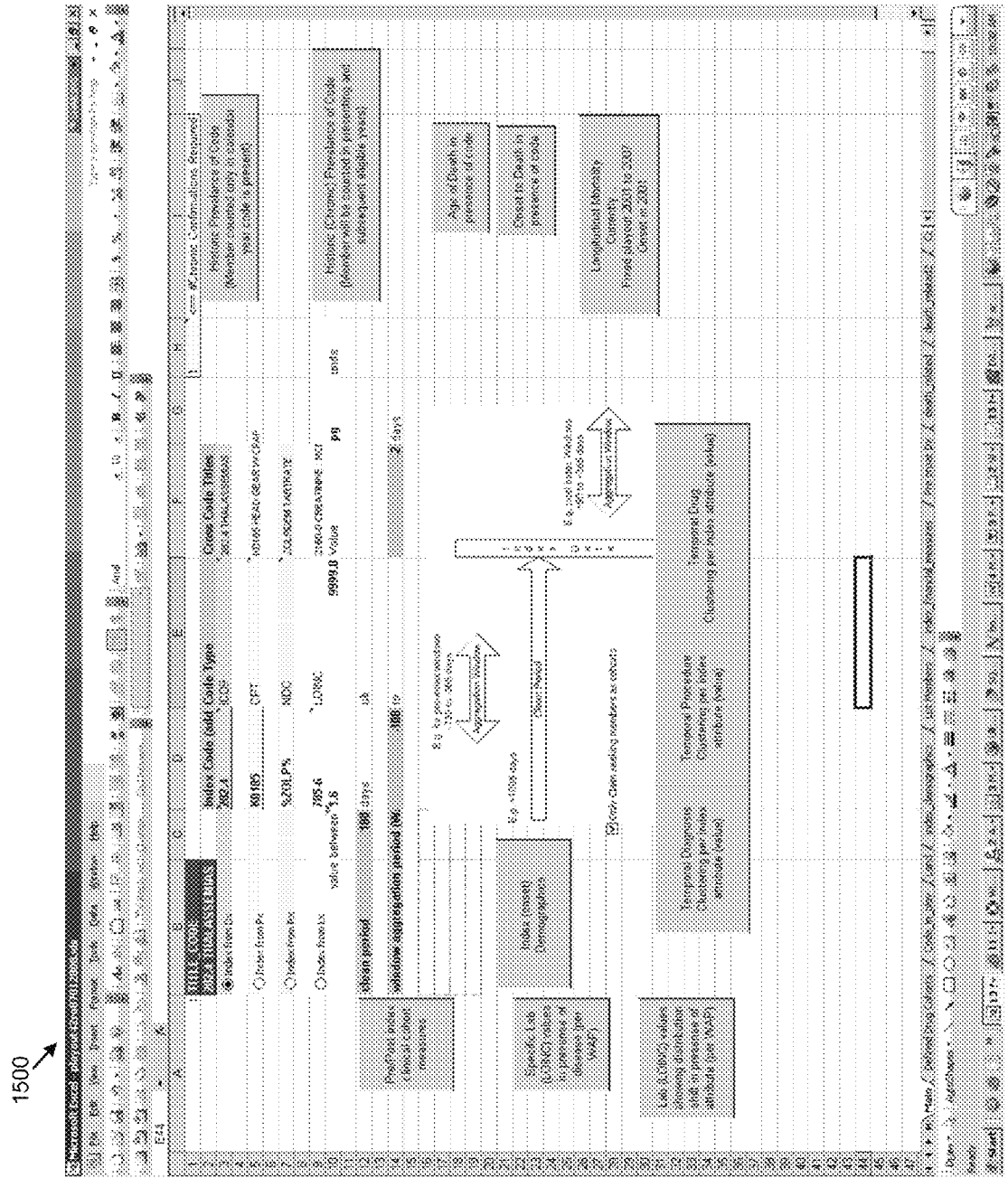
FIG. 15 is a screen-shot diagram illustrating one embodiment of a graphical user interface for rapid assessment of lab value distributions.

FIG. 15 illustrates one embodiment of a graphical user interface (GUI) 1500 for use in accordance with the interface module 502. As illustrated, the GUI 1500 may include one or more fields for receiving user inputs, one or more buttons for issuing a command or controlling the server, application, or code, and one or more descriptive or informational names or elements for providing user instructions and prompts. As illustrated in the informational diagram in FIG. 15, certain limiting criteria or temporal interval may include a clean period value, or time period prior to the occurrence of the medical code. For example, if the medical code is a medical code for diabetes, the clean period criteria may be a time frame, such as two years, before the occurrence of the medical code. In such an embodiment, the first search module 504 may only return records for individuals who have not only been diagnosed with diabetes, but also have a minimum of two years worth of records prior to the diagnosis.

The limiting criteria may also include an aggregation window, or time frame for collecting records associated with the individual. The aggregation window variable may include a time frame before or after the occurrence of the medical code from which to collect records. For example, the filter module 602 may only collect records for two years prior to the occurrence of the medical code and for ninety days after the occurrence of the medical code.

All of the methods disclosed and claimed herein can be made and executed without undue experimentation in light of the present disclosure. While the systems and methods of this invention have been described in terms of preferred embodiments, it will be apparent to those of skill in the art that variations may be applied to the methods and in the steps or in the sequence of steps of the method described herein without departing from the concept, spirit and scope of the invention. In addition, modifications may be made to the disclosed apparatus and components may be eliminated or substituted for the components described herein where the same or similar results would be achieved. All such similar substitutes and modifications apparent to those skilled in the art are deemed to be within the spirit, scope, and concept of the invention as defined by the appended claims.

What is claimed is:

1. A method for comparing two groups of records comprising:
   receiving a medical code;
   searching a database stored on a data storage device to obtain a first group of records associated with individuals having the medical code, wherein each record of the first group of records includes a plurality of test codes, and wherein each of the test codes comprises one or more lab values;
   searching the database to obtain a second group of records associated with a control population, wherein each record of the second group of records includes the plurality of test codes; and
   evaluating a first percentile lab value for each test code of the first group of records representative of each of the one or more lab values of each test code;
   evaluating a second percentile lab value for each test code of the second group of records representative of each of the one or more lab values of each test code, wherein each test code for which a second percentile lab value is evaluated is also a test code in the first group of records;
   determining a relevancy of each test code to the medical code based on the first percentile lab value for each test code and the second percentile lab value for each test code;
   comparing a first percentile lab value representing a particular test code in the first group of records and a second percentile lab value representing the same particular test code in the second group of records; and
   generating an output comprising a distribution graph on a shared scale from the first and second group of records, wherein the output displays the relevancy of each test code to the medical code.

2. The method of claim 1, further comprising interpolating each of the one or more lab values of a particular test code of the plurality of test codes in the first group of records to obtain the first percentile lab value and interpolating each of the one or more lab values of the particular test code of the plurality of test codes in the second group of records to obtain the second percentile lab value, wherein the first and second percentile lab values are associated with a shared percentile lab value.

3. The method of claim 1, wherein generating the output further comprises counting distinct records in the first group of records and the second group of records.

4. The method of claim 1, wherein generating the output further comprises aggregating records from the first group and from the second group according to a selected attribute.

5. The method of claim 4, wherein generating the output further comprises computing a probability in response to a ratio of a number of records in the first group having the selected attribute and a number of records in the second group having the selected attribute.

6. The method of claim 1, further comprising selecting the first group of records from within a time interval.

7. The method of claim 1, wherein the record comprises an average, a first reading or a last reading of a test.

8. The method of claim 1, further comprising selecting records in the first group and in the second group according to a limiting criterion.

9. A system comprising:
a data storage device configured to store a database comprising one or more records, wherein the records include a plurality of test codes, and wherein each of the test codes comprises one or more lab values;
a server in data communication with the data storage device, suitably programmed to:
receive a medical code;
search the database to obtain a first group of records associated with individuals having the medical code, wherein each record of the first group of records includes a plurality of test codes, wherein each of the test codes comprises one or more lab values;
search the database to obtain a second group of records associated with a control population, wherein each record of the second group of records includes the plurality of test codes;
evaluate a first percentile lab value for each test code of the first group of records representative of each of the one or more lab values of each test code;
evaluate a second percentile lab value for each test code of the second group of records representative of each of the one or more lab values of each test code, wherein each test code for which a second percentile lab value is evaluated is also a test code in the first group of records;
determine a relevancy of each test code to the medical code based on the first percentile lab value for each test code and the second percentile lab value for each test code;
wherein the server is further configured to compare a first percentile lab value representing a particular test code in the first group of records and a second percentile lab value representing the same particular test code in the second group of records; and
generate an output comprising a distribution graph on a shared scale from the first and second group of records, wherein the output displays the relevancy of each test code to the medical code.

10. The system of claim 9, wherein the server is further configured to interpolate each of the one or more lab values of a particular test code of the plurality of test codes in the first group of records to obtain the first percentile lab value and to interpolate each of the one or more lab values of the particular test code of the plurality of test codes in the second group of records to obtain the second percentile lab value, wherein the first and second percentile lab values are associated with a shared percentile lab value.

11. The system of claim 9, wherein the server is further configured to count distinct records in the first group of records and the second group of records.

12. The system of claim 9, wherein the server is further configured to aggregate records from the first group and from the second group according to a selected attribute.

13. The system of claim 12, wherein the server is further configured to compute a probability in response to a ratio of a number of records in the first group having the selected attribute and a number of records in the second group having the selected attribute.

14. The system of claim 9, wherein the server is further configured to select the first group of records from within a time interval.

15. The system of claim 9, wherein the server is further configured to select records in the first group and in the second group according to a limiting criterion.

16. A computer program product comprising a non-transitory computer readable medium having computer usable program code executable to perform operations comprising:
receiving a medical code;
searching a database stored on a data storage device to obtain a first group of records associated with individuals having the medical code, wherein each record of the first group of records includes a plurality of test codes, and wherein each of the test codes comprises one or more lab values;
searching the database to obtain a second group of records associated with a control population, wherein each record of the second group of records is identified by includes the plurality of test codes; and
evaluating a first percentile lab value for each test code of the first group of records representative of each of the one or more lab values of each test code;
evaluating a second percentile lab value for each test code of the second group of records representative of each of the one or more lab values of each test code, wherein each test code for which a second percentile lab value is evaluated is also a test code in the first group of records;
determining a relevancy of each test code to the medical code based on the first percentile lab value for each test code and the second percentile lab value for each test code;
comparing a first percentile lab value representing a particular test code in the first group, of records and a second percentile lab value representing the same particular test code in the second group of records; and
generating an output comprising a distribution graph on a shared scale from the first and second group of records, wherein the output displays the relevancy of each test code to the medical code.

17. The computer program product of claim 16, further comprising interpolating each of the one or more lab values of a particular test code of the plurality of test codes in the first group of records to obtain the first percentile lab value and interpolating each of the one or more lab values of the particular test code of the plurality of test codes in the second group of records to obtain the second percentile lab value, wherein the first and second percentile lab values are associated with a shared percentile lab value.

18. The computer program product of claim 16, further comprising counting distinct records in the first group of records and the second group of records.

19. The computer program product of claim 16, further comprising aggregating records from the first group and from the second group according to a selected attribute.

20. The computer program product of claim 19, further comprising computing a probability in response to a ratio of a number of records in the first group having the selected attribute and a number of records in the second group having the selected attribute.

21. The computer program product of claim 16, further comprising selecting the first group of records from within a time interval.

22. The computer program product of claim 16, further comprising selecting records in the first group and in the second group according to a limiting criterion.

* * * * *

UNITED STATES PATENT AND TRADEMARK OFFICE
CERTIFICATE OF CORRECTION

| | |
|---|---|
| PATENT NO. | : 8,429,186 B2 |
| APPLICATION NO. | : 12/774270 |
| DATED | : April 23, 2013 |
| INVENTOR(S) | : David R. Anderson |

Page 1 of 1

It is certified that error appears in the above-identified patent and that said Letters Patent is hereby corrected as shown below:

In the Claims:

In claim 16, column 22, line 31, delete "is identified by".

In claim 16, column 22, line 32, delete "and".

Signed and Sealed this
Twenty-first Day of May, 2013

Teresa Stanek Rea
*Acting Director of the United States Patent and Trademark Office*